United States Patent [19]

Mast et al.

[11] Patent Number: 4,751,935
[45] Date of Patent: Jun. 21, 1988

[54] ARTIFICIAL FINGERNAIL

[75] Inventors: Rolf Mast; Richard C. G. Dark, both of San Bernadino, Calif.

[73] Assignee: Lee Pharmaceuticals, South El Monte, Calif.

[21] Appl. No.: 36,499

[22] Filed: Apr. 9, 1987

[51] Int. Cl.[4] ............................................ A45D 40/30
[52] U.S. Cl. ...................................... 132/88.5; 132/73
[58] Field of Search ........................ 132/88.5, 88.7, 73

[56] References Cited

U.S. PATENT DOCUMENTS

| | | | |
|---|---|---|---|
| 1,942,332 | 1/1934 | Hamberg | 132/73 |
| 2,746,460 | 5/1956 | Jellinek | 132/73 |
| 2,816,555 | 12/1957 | Klump | 132/73 |
| 4,007,748 | 2/1977 | Matranga et al. | 132/73 |
| 4,060,081 | 11/1977 | Yannas et al. | 128/156 |
| 4,085,466 | 4/1978 | Goodfellow et al. | 3/1.91 |
| 4,135,526 | 1/1979 | Matranga et al. | 132/73 |
| 4,280,954 | 7/1981 | Yannas et al. | 260/123.7 |
| 4,350,629 | 9/1982 | Yannas et al. | 260/123.7 |
| 4,378,224 | 3/1988 | Nimni et al. | 8/94.11 |
| 4,407,310 | 10/1983 | Jaduw | 132/73 |
| 4,448,718 | 3/1984 | Yannas et al. | 260/123.7 |
| 4,502,161 | 5/1985 | Wall | 3/1.91 |
| 4,552,160 | 11/1985 | Griggs | 132/73 |

OTHER PUBLICATIONS

Smillie, (1943) British J. Surg. 398–402.
Bullough et al., (1970) J. Bone Joint Surg. 52B:564–570.
Cox and Cardell, (1977) Clin. Orthopaed. Related Res. 125:236–242.
Seedham (1979) Engin. Med. 8:207–219.
Arnoczky and Warren, (1983) J. Sports Med. 11:131–141.
Arnoczky, *Advances in Orthopaedic Surgery.*, by the Williams and Wilkins Co., pp. 244–252.
Arnoczky et al. (1986) 32nd Ann. ORS, New Orleans, Louisiana, p. 452.
Milachowski et al. (1986) Orthopadischem Klinik, Klinikum Grosshadern, Munchen. z. Orhop. (Jul.–Aug. 1986) 124:508–512.
Reaupre' et al. (1986) Clin. Orthopaed. Related Res. 208:72–75.
Ahmed "Load-Carrying Characteristics of Meniscus and Tibial Plateau—A Review of Recent Results".

*Primary Examiner*—Gregory E. McNeill
*Attorney, Agent, or Firm*—Ronald M. Goldman; W. Norman Roth

[57] ABSTRACT

An artificial fingernail or tip formed of polymer plastic contains light diffusing means located only within the front distal portion, the light diffusing means including, a plurality of minute depressions within and throughout at least the upper surface of said polymer strip for providing a textured roughened surface to obtain a natural appearing contrast between the front distal portion and the back proximal portion of the nail. In an additional aspect, the appearance is further enhanced by inclusion of slight pigmentation of the plastic material.

19 Claims, 1 Drawing Sheet

U.S. Patent  Jun. 21, 1988  4,751,935
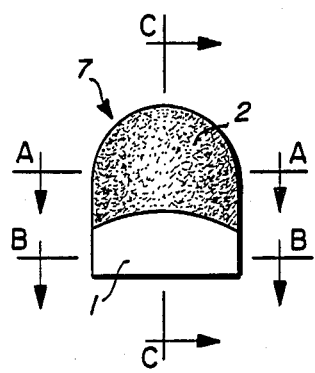
FIG_1
FIG_2a
FIG_2b
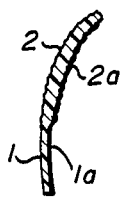
FIG_2c
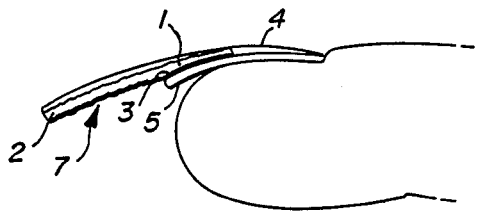
FIG_3
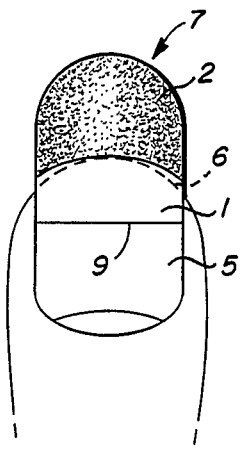
FIG_4
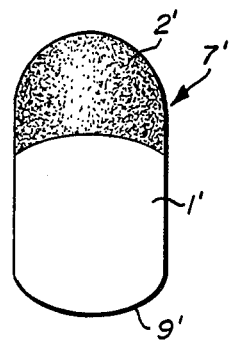
FIG_5

ARTIFICIAL FINGERNAIL

FIELD OF THE INVENTION

This invention relates to fingernail decorations and, more particularly, relates to artificial fingernails and fingernail extensions.

BACKGROUND

A part of the human anatomy which has benefited from the attention of the modern cosmetics industry is the fingernail. Carefully manicured and brightly painted fingernails of great length are a necessary part of the wardrobe of decorations that complete the portrait of femininity, good grooming, and great beauty of the modern woman. Consequently a great deal of time is spent applying nail polish to and admiring long fingernails. The demands of the working world deprive many women of the opportunity to allow their fingernails to grow to great length. The work a day world of chores results in broken nails or stress induced chewed down fingernails.

One solution to this "short nail" problem is the cosmetic decoration referred to as artificial fingernails that either cover the natural nail entirely or form extensions or "tips" as they are sometimes called that are attached to the front or distal end of the fingernail. The attachment of a plastic strip, generally shaped and sized to resemble a fingernail of extended length, to the distal end of the natural fingernail is a known technique and structure for cosmetically extending the length of a natural fingernail. Typically these simulations take the form of sheets or strips, as variously termed, of injection molded plastic material attached by an undersurface using glue, such as ethylcyanoacrylate based glue, to the natural fingernail. They are commercially available in a variety of between six to thirteen widths, corresponding to the width of human fingernails, and possess a curvature such that the underside concave surface of the nailtip in a side to side direction generally matches the upper convex surface of the natural nail to allow a reasonably matching fit therebetween. The tips are available generally by choice in lengths of between 0.3 inches to 1.5 inches and many are curved in a longitudinal direction to simulate the downward curvature of a naturally growing fingernail.

Nail extensions are commonly attached by professional manicurists. Typically a plastic strip in the general form of the human nail is glued to the tip of a natural nail and in that position the strip extends beyond the fingertip by the distance selected. An acrylic coating, which is essentially clear or colorless, is then applied over the upper surface of the strip, much like applying nail polish, and the uncovered portion of the fingernail and the coating is allowed to cure. Gluing a strip on the top surface of the natural nail more often than not leaves a ridge, which must be removed. This is accomplished by filing the ridge down until it disappears or by applying a top coating to cover or hide the ridge or a combination of both techniques with varying result. Thus any ridge lines that appear between the rear edge of the tip and the fingernail upon completion of the procedure above described are filed down to provide an even surface. Additional acrylic coatings are applied as necessary and additional filing or trimming is undertaken as necessary to achieve the attractive natural looking smooth surface. This procedure requires effort, patience and good technique.

Artificial fingernails that serve as extensions to the natural fingernails and the application of those extensions are disclosed in U.S. Pat. No. 4,007,748 granted Feb. 15, 1977 to Matranga et. al. and in U.S. Pat. No. 4,135,526 granted Jan. 23, 1979 also to Matranga et. al. In the former patent Matranga discloses the gluing of the nail extension to the leading or distal edge of the nail and the filling and filing of any ridges. The edge to edge structure appears fragile and appears to require careful alignment. In the latter patent Matranga discloses an extension formed with a stop ridge on the under surface so that the leading edge of the natural fingernail slides into the stop, which contains an adhesive, and a portion of the proximal end of the extension overlaps a portion of the natural fingernail, which leaves a slight ridge. The ridge is then filed down to create a smooth transition between the two surfaces. The creation of and appearance of the ridge and its visual elimination is a complication to the use of existing fingernail tips. Because the overlap type appears easier to install and offers better physical support it is generally preferred in the inventors view.

Some commercially available nailtips of the overlap type of which the Matranga et. al. patent is illustrative deliniate the overlap area by a change in thickness of the plastic strip. In general the distal edge of this overlap area is the same general shape as the distal edge of the nailbed. Thus the thickness of many commercial nailtips is reduced along a curved line to correspond to the edge of the finger with the nail in place. This reduced thickness portion, which extends proximally beyond this curved line, is, typically, in the range of 0.003 inches to 0.016 inches. The distal portion of the fingernail extension is usually in the range of 0.015 inches to 0.030 inches in thickness. Other commercially available nailtips do not have a sharply defined overlap area and are of either fairly uniform thickness or have a gradually taper in which the thickness of the nail tapers from thick, at the distal end, to thin on the overlap area.

Examination of an extended natural fingernail shows that the apparent color of the nail changes as it grows beyond the distal edge of the fingers nail bed. The appearance is of a color change going from clear to milky. Even if the tip is pigmented correctly and looks natural beyond the fingernail itself, in the overlap area, as above described in which a portion of the tip overlaps the natural nail, it is still possible to detect the change in coloring as might be regarded as unnatural. And if a clear artificial nail tip is used, the overlap area looks natural, but the extended area appears too clear; and, hence, may appear unnatural. The distinctions in appearance may in reality be regarded as subtle by some. Nonetheless the person who wears the artificial nails becomes aware of the problem and as a consequence of that notice the problem may grow out of proportion in that persons mind.

An object of the invention, therefor, is to provide an improved more natural appearing artificial fingernail extension of the overlap type. It is a further object to provide a fingernail tip assembly which minimizes the creation of ridges and is thereby more easily installed. It is a still further object of the invention to provide an artificial fingernail that closely duplicates and simulates the coloring change as appears in a natural fingernail between the nail portions overlying the fingers nail bed and that portion which extends beyond the distal portion of the nail bed. A further object of the invention is to provide a new mold structure for achieving more natural looking artificial fingernails by injection molding processes.

The invention is characterized by a fingernail portion simulating strip means of molded polymer material of the type having a size and geometry for attachment to a natural fingernail to simulate at least a portion of an overgrown natural fingernail of a length that extends beyond the tip of the finger supporting the natural fingernail, said strip containing surfaces, including an upper surface and a bottom surface, and front distal and back proximal portions to said surfaces, said distal portion corresponding to and simulating the whitish colored portion of a natural nail that extends beyond the finger cuticle and said proximal portion corresponding to and simulating at least a portion of a natural fingernail that overlies the cuticle, the improvement therein comprising: light diffusing means located only within and covering said front distal portion for diffusing light incident on said front distal portion of the surface of said strip, said light diffusing means including, a plurality of minute depressions within at least the upper surface of said polymer strip for providing a textured roughened surface, to obtain a natural appearing contrast in appearance between the front distal portion and the back proximal strip portion. the finger supporting the natural fingernail, said strip containing a surface, including an upper surface and a bottom surface, and front and back ends, the improvement therein comprising: light diffusing means for diffusing light.

The foregoing objects and advantages of the invention together with the structure characteristic of the invention, which was only briefly summarized in the foregoing passage, becomes more apparent to those skilled in the art upon reading the detailed description of a preferred embodiment of the invention, which follows in this specification, taken together with the illustrations thereof presented in the accompanying drawings.

BRIEF DESCRIPTION OF THE DRAWINGS

In the Drawings:

FIG. 1 illustrates a fingernail extension constructed according to the invention in a top plan view;

FIG. 2a is a section view of the embodiment of FIG. 1 taken along section lines A—A;

FIG. 2b is a section view of the embodiment of FIG. 1 taken along section lines B—B;

FIG. 2c is a section view of the embodiment of FIG. 1 taken along the section lines C—C to show the profile of the embodiment along its longitudinal axis;

FIG. 3 is a profile or side view of the embodiment of FIG. 1 as combined with the natural fingernail in an assembly according to the invention;

FIG. 4 is a top plan view of the assembly of FIG. 3; and

FIG. 5 is a top plan view of a second embodiment of the invention in the form of a complete nail.

DETAILED DESCRIPTION

In FIG. 1 a fingertip extension 7 is illustrated in top plan view and consists of a plastic sheet or strip in the general shape of a natural fingernail. This strip contains two portions and is thus "mapped" into two contiguous surface areas; the proximal section or portion 1 and the distal portion 2. As shown the proximal portion is of a polished or smooth surface characteristic. The distal portion is textured or roughened in appearance, as represented by the speckling in the illustration, forming a large number of microscopic surface indentations. Effectively the strips distal portion 2 contains an incident light diffuser.

As further illustrated in the cross section view of FIG. 2a, the preferred embodiment contains the textured surface on the upper surface and also contains the same textured surface 2a on the underside surface as well. The two textured surfaces occupy the same portion of the distal area of the tip and overlye one another; hence, the two textured surfaces are congruent in this embodiment. Further as shown in the section view of FIG. 2b, which is a cross section view taken along the lines B—B in FIG. 1, the area of the strip underlying the polished surface area 1 is also polished in this preferred embodiment and is identified by 1a. And the proximal portion is of a lesser thickness than the distal portion 2. The general shape of the plastic strip is that of the extended portion of a human fingernail with an inside concave curvature to generally match the curvature of a nail and a longitudinal curvature as depicted in the section view of FIG. 2c.

In FIG. 2c, which represents a cross section view of plastic strip 7 in FIG. 1, taken along the section lines C—C which coincides with the longitudinal axis of the strip, the nail extension is shown to curve to resemble the natural curvature of an overhang portion of a natural nail which is overgrown. The figure also better illustrates the difference in thickness between the two sections or portions. In as much as this embodiment is a fingertip of the overlap type, the thin rear portion is intended for placement over a more thick natural nail. Ideally the thin portion 1 is tapered to be as thin as possible so as to minimize the possibility of visible ridge formation between the proximal edge of the tip and the natural fingernail when installed, as discussed in the background to this invention, and still be consistent with the requirements of injection molding.

The strip is molded of a transparent plastic material. The plastic is of a composition that undergoes the injection molding process with a resultant clear appearance or one which is only faintly milky in thicknesses of between 0.003 inches to about 0.012 inches. Suitable polymers are cellulose acetate and other cellulosic esters, nylon, clear acrylonitrile butadiene styrene copolymer, acrylic resin, and polystyrene.

A dye or pigment, as variously termed is included within the plastic in this embodiment and enhances the appearance of the strip. Many pigments may be used. Acceptable pigments by way of example are titanium dioxide, titanium dioxide coated mica, which is a pearlescent material, and zinc oxide. Other coloring agents may be used and mixtures of pigments can be used to tailor the appearance to ones desired color, recognizing the different colorations between human beings of different races and nationality, all of whom should find this nail of use. Suitable concentrations of pigment used in the plastic matrix are in the range of zero or trace amounts to and including twenty grams for each three pounds U.S. of resin, with preferred concentrations in the range of 0.5 grams to and including ten grams for every three pounds of resin. In one specific example approximately 0.7 grams of dye MC 21080 supplied by Marco Color Labs company was added to one U.S. pound of plastic resin to obtain a slight pearl colored tint to the plastic as molded.

Distal portion 2 of the plastic strip in FIG. 1 is more opaque in appearance due to the light diffusion characteristic of the rough surface on the uppper surface and the congruent area on the undersurface. In addition because front portion 2 of the strip is more thick than rear proximal portion 1, there is more pigment in this area, which adds to the opaqueness. On the other hand the rear overlap portion has a smooth polished surface and appears more transparent. This provides contrast between the two portions. It also provides a natural appearance as installed. The thickness may vary. By way of specific example the thick distal portion 2 is of a thickness in the range of 0.015 inches to 0.035 inches; the proximal thin portion 1 is of a thickness in the range of 0.003 inches to 0.020 inches.

Plastic strip 7 is installed in place attached to a natural fingernail as illustrated in FIG. 3. Rear proximal section 1 is attached overlying the natural nail 5 by means of adhesive 3, suitably a conventional compound earlier described and also known as "instant" glue or "crazy" glue. This is followed by an overcoating 4 of a semi-transparent coating material, such as vinyl which is allowed to cure. At this stage reference may be made to FIG. 4 which shows the relative position of the tip and thin proximal section 1 in a top plan view prior to the application of the vinyl coating, not illustrated in this figure. The curvature of the natural nails distal edge is illustrated by phantom line 6. The combination of the semi translucent finishes of plastic strip 7 and the acrylic coating 4 combine to make a very natural appearing human nail extentsion, effectively concealing the line or juncture of the proximal edge 9 of the plastic strip.

Although I have illustrated the fingernail extension in FIGS. 1 and 4 as having a rounded distal peripheral edge, it is understood that other shapes may be chosen instead according to dictates of current fashion. One other peripheral edge shape in current use is a flat front edge; another is more pointed. As those skilled in the art of fashion are aware many new and experimental shapes may be substituted.

The incorporation of a texture formed by minute depressions in the surface of the polymer plastic strip forming an artificial fingernail, accomplished in a molding process, is not new, where employed as a marker. An artificial fingernail marketed by the Lee Pharmaceutical Company of South El Monte, Ca., an assignne of a partial interest of the present application, as the "Press on" nail as product Catalogue No. 7617-0000 is formed of a polymer plastic material that contains an intese pigmentation, providing a nail of solid color and attractive appearance. That artificial nail also contains a plurality of minute depressions in the proximal underside surface of the fingernail to roughen or texture the surface at that location. And, according to the accompanying instructional application material, the roughened surface serves as an indicium or marker informing the user which end of the plastic strip is the proximal end. So doing minimizes application errors by those would might be less observant. After the artificial nail was installed, for example by gluing, the proximal portion is placed over the natural fingernail and the existence of the indicium is obscured and is not noticeable, which permitted use of such a textured portion as a directional marker. In one sense Applicant has discovered that the roughened surface of the "Press on" nail can be changed in size and position and applied to a different purpose in a noticeable position rendering a more attractive natural looking nail, particularly those nails known as "French tips".

The installation of the light diffuser into the plastic strip is accomplished with a new mold construction. The injection molds are of conventional material, such as steel, and are formed in two parts, which define a mold cavity having the outer shape of the plastic part defined by the shape and size of the cavity walls or surfaces. This structure and process are well known. In accordance with the invention the cavity surfaces have different surface finishes corresponding to the two different surfaces described for the fingernail extension. In the second area, corresponding to the proximal area of the fingernail, the surface is constructed to a finish corresponding to SPI/SPE Mold Standard no. one or two. In the first area, corresponding to the distal area of the fingernail, the surface is constructed to a finish corresponding to SPI/SPE Mold Standard no. six. Mold standards 1 and two provide that the mold cavity is polished with diamond dust compounds to achieve a high lustre to the cavity surface. Mold standard no. 6 allows for a rougher surface finish or "texture" which is attained through sand blasting of the surface with a fine grain sand material. Specifically the standards are given as follows:

Standard 1 8000 grit no. 3 micron range diamond.
Standard 2 1200 grit no. 5 micron range diamond.
Standard 6 24 grit dry blast at 3 inch distance and 100 lbs. pressure 54–56 rc when blasted.

The proximal surface area of the mold cavity is covered while the distal area is being polished to the rough texture to protect the highly polished proximal area.

The term texture, as it is used herein, is intended to denote a roughening of the surface or appearance of a series of minute microscopic depressions that will dull the appearance of the surface in contrast to a smooth polished surface. An analogy applicable to the mold surface and the artificial fingernail is the contrast between a clear glass window and one which is frosted to occlude the view. In this definition the clear window is polished or smooth and the frosted one is textured.

The incorporation of a light diffuser within the plastic strip forming a fingernail extension as described in connection with the preceeding embodiments of the invention, finds application as well in a complete covering nail. Thus as an example FIG. 5 illustrates a top plan view of the artificial fingernail incorporating the light diffuser. For convenience, the elements that are common to both embodiments are identified by the same numeral with an added prime mark. As shown the rear polished portion 1' of strip 7' is greater in length than the corresponding element of the tip in FIG. 1 and it has a rounded or shaped rear proximal edge. Since this fingernail covers the entire surface of the natural fingernail its proximal edge generally conforms to the shape of the rear of the fingers fingernail bed. Further proximal portion 1' in this embodiment is of the same essential thickness as the distal portion 2' and thus the plastic strip may be of generally uniform thickness. Since this embodiment covers the entire surface of the natural nail there is no ridge problem as is encountered with fingernail extensions. Suitable thickness of this strip is in the range of 0.008 inches to 0.035 inches with 0.020 inches preferred.

The nail of FIG. 5 is installed in place overlying the natural nail by glue as described or with an intermediate glue pad, not illustrated, which fits between the natural nail and the articial one, adhering to the upper surface of the former and the undersurface of the latter.

In the preceding description the invention has been discussed in connection with a single artificial nail. However it is understood that in practice commercially groups of nails are marketed in a packet with many sizes.

It is believed that the foregoing description of the preferred embodiments of the invention is sufficient in detail to enable one skilled in the art to make and use the invention. However, it is expressly understood that the detail of the elements which are presented for the foregoing purpose is not intended to limit the scope of the invention, in as much as equivalents to those elements and other modifications thereof, all of which come within the scope of my invention, will become apparent to those skilled in the art upon reading this specification. Thus the invention is to be broadly construed within the full scope of the appended claims.

What is claimed is:

1. In a fingernail portion simulating strip means of molded polymer material of the type having a size and geometry for attachment to a natural fingernail to simulate in shape at least a portion of an overgrown natural fingernail of a length that extends beyond the tip fo the finger supporting the natural fingernail, said strip containing surfaces, including an upper surface and a bottom surface, and front distal and back proximal portions to said surfaces, said distal portion corresponding in position to the whitish colored portion of a natural nail that extends beyond the finger cuticle and said proximal portion corresponding in position to at least a portion of a natural fingernail that overlies the cuticle, the improvement which comprises: light diffusing means located only within and covering said front distal portion for diffusing light incident on said front distal portion of the surface of said strip means said light diffusing means including a plurality of minute depressions within at least the upper surface of said polymer strip means for roughening said surface, to provide a natural appearing contrast in appearance between the front distal portion, which is relatively dull, and the back proximal strip portion, which is bright relative to said distal portion, whereby to simulate in appearance a natural fingernail.

2. The invention as defined in claim 1 wherein said plurality of depressions includes a first portion of said depressions being located within and covering the upper surface of said strip in the front distal portion only and a second portion of said depressions being located within and covering the bottom surface of said strip in the front distal portion only.

3. The invention as defined in claim 1, further comprising: coloring means included within said polymer strip material for lightly coloring said strip and wherein said coloring means comprises a pigment, said pigment being of a concentration in the range of 0.1 to 20 grams of pigment for each three U.S. pounds of polymer resin.

4. The invention as defined in claim 1, further comprising: attaching means for attaching said strip to the tip of a natural fingernail.

5. The invention as defined in claim 1, further comprising: attaching means for attaching said strip in a position on and overlying essentially entirely a natural fingernail for covering the upper surface of said natural fingernail.

6. Artificial fingernail means for attachment to a natural fingernail to simulate a natural fingernail of a length sufficient to extend beyond the tip edge of the finger supporting such natural fingernail in which the distal portion possesses a more whitish coloration tahn the proximal portion, said means comprising strip means of molded polymer material of a predetermined surface area, including an upper surface and a lower surface; said strip means containing first and second portions located adjacent one another and representing the distal and proximal portions, respectively, of a natural nail; said first portion of said surface area containing thereover minute depressions within said polymer material to provide a roughened textured surface characteristic for diffusing light incident on said first portion, and said remaining second portion of said surface containing a smooth surface characteristic for reflecting light incident thereon differently than light reflected by said portion containing said depressions to simulate the natural difference in coloration in a natural nail between the more whitish coloration of the distal portion overhanging the finger and the proximal portion above the cuticle.

7. The invention as defined in claim 6 wherein said first portion of said surface is located on said underside surface at a position there along contiguous with said front edge.

8. The invention as defined in claim 6 wherein said first portion of said surface is located on said underside surface at a position there along contiguous with said front edge and wherein a remaining part of said first portion is located on said upper surface at a position thereamong overlying said first part of said first portion, said first and second parts of said first portion being essentially equal in area.

9. The invention as defined in claim 6 including: means for attaching said strip to the tip edge of a natural fingernail to provide an extension thereto, whereby a portion of the natural fingernail remains uncovered by said strip.

10. The invention as defined in claim 6 including: means for attaching said strip in a position overlying and covering a natural fingernail to provide a simulated fingernail.

11. The invention as defined in claim 6; in which said strip further contains: coloring means within said polymer material for coloring said strip.

12. The invention as defined in claim 8 in which said strip has a thickness in the range of 0.015 inches to 0.035 inches and is non-uniform in thickness, said overlap second portion of said strip being in the range of 0.003 inches to and including 0.020 inches in thickness.

13. The invention as defined in claim 6 wherein said strip comprises a predetermined thickness in the range of 0.008 to 0.035 inches and said thickness is uniform.

14. The invention as defined in claim 6 in which said strip has a thickness in the range of 0.015 inches to 0.035 inches and is non-uniform in thickness, said overlap second portion of said strip being in the range of 0.003 inches to and including 0.020 inches in thickness.

15. The invention as defined in claim 11 wherein the said coloring material comprises a pigment, said pigment being of a concentration in the range of 0.1 to 20 grams of pigment for each three U.S. pounds of polymer resin.

16. The invention as defined in claim 11 wherein said coloring material comprises a pigment, said pigment being of a concentration within the range of 0.5 grams to 10.0 grams of pigment for each three pounds U.S. of resin material.

17. The invention as defined in claim 1 wherein said strip means comprises a predetermined thickness in the range of 0.008 to 0.035 inches and said thickness is uniform.

18. The invention as defined in claim 1 in which said strip means has a thickness in the range of 0.015 inches to 0.035 inches and is non-uniform in thickness, and said light reflecting portion of said strip being of a thickness in the range of 0.003 inches to and including 0.020 inches.

19. The artificial fingernail resulting from the process of injection molding a mixture of polymer plastic material and pigment into a mold; said mold containing a mold cavity, and said cavity containing a surface wall in the geometry of an artificial nail of predetermined size and shape; said surface wall having a first surface portion of a highly polished surface characteristic and corresponding in geometry to the proximal portion of a natural fingernail and said surface wall having a second surface portion adjacent to said first surface portion of a rough textured surface characteristic and corresponding in geometry to the distal portion of a natural fingernail, said first portion of said mold wall surface being of a surface finish defined by SPI/SPE mold standard No. 6 and said second portion being of a surface finish defined by SPI/SPE mold standard no greater than No. 2; and said pigment being of a concentration within the range of 0.5 grams to 10.0 grams of pigment for each three pounds U.S. of resin material.

* * * * *